United States Patent
Batycky et al.

(10) Patent No.: US 9,295,661 B2
(45) Date of Patent: Mar. 29, 2016

(54) METHODS FOR REDUCING INTER-PATIENT VARIABILITY OF LEVODOPA PLASMA CONCENTRATIONS

(71) Applicant: CIVITAS THERAPEUTICS, INC., Chelsea, MA (US)

(72) Inventors: Richard P. Batycky, Newton, MA (US); Martin Freed, Wellesley, MA (US)

(73) Assignee: Civitas Therapeutics, Inc., Chelsea, MA (US)

( * ) Notice: Subject to any disclaimer, the term of this patent is extended or adjusted under 35 U.S.C. 154(b) by 0 days.

(21) Appl. No.: 14/691,788

(22) Filed: Apr. 21, 2015

(65) Prior Publication Data

US 2016/0015663 A1    Jan. 21, 2016

Related U.S. Application Data

(63) Continuation of application No. PCT/US2013/065834, filed on Oct. 21, 2013.

(60) Provisional application No. 61/716,753, filed on Oct. 22, 2012.

(51) Int. Cl.
| | |
|---|---|
| *A61K 31/198* | (2006.01) |
| *A61K 9/00* | (2006.01) |
| *A61K 45/06* | (2006.01) |
| *A61K 47/24* | (2006.01) |
| *A61K 47/02* | (2006.01) |

(52) U.S. Cl.
CPC ............. *A61K 31/198* (2013.01); *A61K 9/0075* (2013.01); *A61K 45/06* (2013.01); *A61K 47/02* (2013.01); *A61K 47/24* (2013.01)

(58) Field of Classification Search
None
See application file for complete search history.

(56) References Cited

U.S. PATENT DOCUMENTS

| 7,556,798 B2 | 7/2009 | Edwards et al. |
| RE43,711 E | 10/2012 | Jackson et al. |

FOREIGN PATENT DOCUMENTS

| GB | 2454480 A | 5/2009 |

OTHER PUBLICATIONS

Bartus, et al., "A Pulmonary Formulation of L-Dopa Enhances its Effectiveness in a Rat model of Parkinson's Disease," Journal of Pharmacology and Experimental Therapeutics, 310(2):828-835, 2004.

*Primary Examiner* — Kristin Vajda
(74) *Attorney, Agent, or Firm* — Elmore Patent Law Group, P.C.; Carolyn S. Elmore; Darlene A. Vanstone

(57) ABSTRACT

The present invention provides methods of reducing the inter-patient variability of levodopa plasma concentrations in a population of Parkinson's disease patients. The methods of the invention comprise pulmonary administration of levodopa at therapeutically effective concentrations such that the inter-patient variability of levodopa plasma concentrations at time periods ranging from about 10 minutes post inhalation to about 60 minutes or more post inhalation have less than a 50% coefficient variation. The methods of the invention are particularly useful for treatment of motor fluctuations which arise as a side effect of L-Dopa therapy.

26 Claims, 8 Drawing Sheets

METHODS FOR REDUCING INTER-PATIENT VARIABILITY OF LEVODOPA PLASMA CONCENTRATIONS

RELATED APPLICATIONS

This application is a continuation of International Application No. PCT/US13/65834, which designated the United States and was filed on Oct. 21, 2013, published in English, which claims the benefit of U.S. Provisional Application No. 61/716,753, filed Oct. 22, 2012. The entire teachings of the above application are incorporated herein by reference.

BACKGROUND OF THE INVENTION

Parkinson's disease is characterized neuropathologically by degeneration of dopamine neurons in the basal ganglia and neurologically by debilitating tremors, slowness of movement and balance problems. It is estimated that over one million people suffer from Parkinson's disease. Nearly all patients receive the dopamine precursor levodopa or "L-Dopa", often in conjunction with the dopa-decarboxylase inhibitor, carbidopa. L-Dopa adequately controls symptoms of Parkinson's disease in the early stages of the disease. However, it tends to become less effective after a period which can vary from several months to several years in the course of the disease.

One example of L-Dopa's diminishing effectiveness is the development of motor fluctuations in a subject undergoing treatment. By "motor fluctuations" it is meant that a subject begins to show a variable response to dopamine replacement therapy such that for periods of time the therapeutic agents exhibit good efficacy whereas for other periods of time the agents appear to have little effect. Motor fluctuations can manifest as a 'wearing-off' of efficacy, the efficacy of L-Dopa therapy does not last as long as initially observed, and an 'on-off' syndrome where the patient experiences disabling fluctuations in mobility ensues. Gradually, over a period of time, the efficacy of L-Dopa (so called "on-time") may be reduced to the extent that the usefulness of dopaminergic treatments becomes severely limited.

It is believed that the varying effects of L-Dopa in Parkinson's disease patients are related, at least in part, to the plasma half life of L-Dopa which tends to be very short, in the range of 1 to 3 hours, even when co-administered with carbidopa. In the early stages of the disease, this factor is mitigated by the dopamine storage capacity of the targeted striatal neurons. L-Dopa is taken up and stored by the neurons and is released over time. However, as the disease progresses, dopaminergic neurons degenerate, resulting in decreased dopamine storage capacity.

Accordingly, the positive effects of L-Dopa become increasingly related to fluctuations of plasma levels of L-Dopa. In addition, patients tend to develop problems involving gastric emptying and poor intestinal uptake of L-Dopa. Erratic gastric emptying of levodopa contributes to random fluctuations in mobility. Patients exhibit increasingly marked swings in Parkinson's disease symptoms, ranging from a return to classic Parkinson's disease symptoms, when plasma levels fall, to the so-called dyskinesis, when plasma levels temporarily rise too high following L-Dopa administration.

Controlling plasma fluctuations of levodopa in a patient and between patients would eliminate variability in clinical responses across a patient population thereby providing doctors and patients with a more reliable therapeutic treatment regimen for the disease. Therefore, a need exists for new treatment regimens that reduce inter-patient variability in plasma concentrations and patient responses in patients suffering from Parkinson's disease.

SUMMARY OF THE INVENTION

The present invention provides methods of reducing the inter-patient variability of levodopa plasma concentrations in a population of Parkinson's disease patients. The methods of the invention comprise pulmonary administration of levodopa at therapeutically effective concentrations such that the inter-patient variability of levodopa plasma concentrations at time periods ranging from about 10 minutes post inhalation to about 60 minutes or more post-inhalation have less than a 50% coefficient variation. The methods of the invention are particularly useful for treatment of motor fluctuations which arise as a side effect of L-Dopa therapy.

DETAILED DESCRIPTION OF THE INVENTION

Definitions

Figure 1:
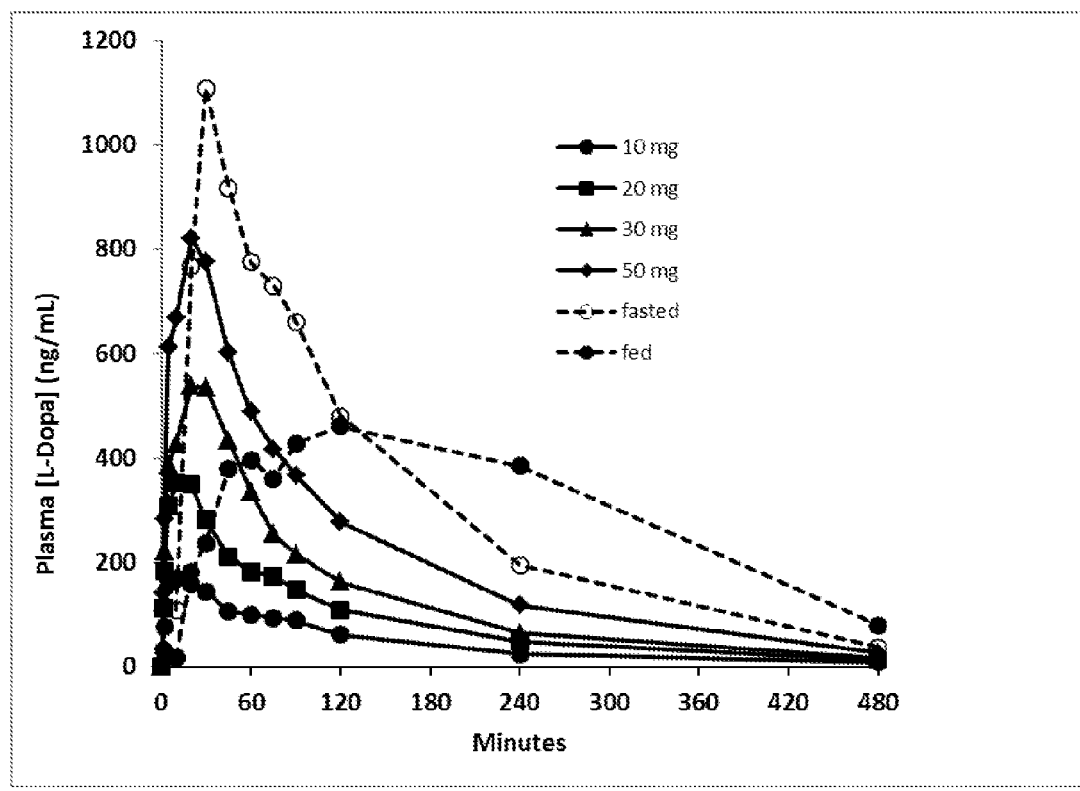
FIG. 1: Mean plasma levodopa concentration vs. time data following 90/8/2 inhalation and oral levodopa administration.

The half-life time $T_{1/2}$ is the time for a concentration C of a drug in a body fluid or a tissue to reach the concentration C/2.

The area under the curve, AUC, corresponds to the integral of the plasma concentration over a given time interval. The AUC is expressed in units of mass (mg, g)×liter−1×hour, and is a measure of the bioavailability of a drug.

The term "coefficient of variation" (CV) which is expressed as % CV, is defined as the ratio of the standard deviation σ to the mean μ:

$$C_v = \sigma/\mu$$

As used herein, the phrase "nominal dose" or "nominal powder dose" means the percentage of levodopa which is present in the total mass of particles contained in the receptacle and represents the maximum amount of levodopa available for administration to the patient.

The fine particle fraction" or "FPF" corresponds to the percentage of particles in the mass of particles present in the receptacle that have an aerodynamic diameter of less than 5.6 μm.

The term "fine particle dose" as used herein is defined as the nominal dose multiplied by the FPF.

"$Cmax^{Pul}$" means the maximum observed plasma concentration (Cmax) as measured after pulmonary delivery. "$Cmax^{oral}$" means the maximum observed plasma concentration as measured after oral delivery.

"$AUC^{Pul}$" means the area under the plasma concentration versus time curve (AUC) as measured after pulmonary delivery. "$AUC^{oral}$" means the area under the plasma concentration versus time curve (AUC) as measured after oral delivery.

LIST OF ABBREVIATIONS

A y-axis intercept for distribution phase
α Distribution phase rate constant
AUC Area under the plasma concentration versus time curve
$AUC_{0-t}$ AUC from time 0 to last measureable plasma concentration
$AUC_{0-\infty}$ AUC from time 0 to infinity
$AUC_{0-10m}$ AUC from time 0 to 10 minutes
B y-axis intercept for elimination phase
β Elimination phase rate constant
BLQ Below Level of Quantitation (of the assay)
C y-axis intercept for absorption phase
CD/LD Carbidopa/levodopa
CL/F Clearance divided by fraction of drug absorbed
$C_{max}$ Maximum observed plasma drug concentration
$C_{max,10m}$ $C_{max}$ observed in first 10 minutes
FPD Fine particle dose
K01 Absorption rate constant
K10 Elimination rate constant, PK model
K12 Inter-compartmental rate constant, compartment 1→2
K21 Inter-compartmental rate constant, compartment 2→1
λ Elimination rate constant
LD Levodopa
L-Dopa Levodopa
mg Milligrams
min Minutes
mL Milliliters
NC Not calculated
NCA Non-compartmental PK analysis
ng Nanograms
NS No sample
PD Parkinson's disease
PK Pharmacokinetic
$T_{1/2}$ Terminal half-life
$T_{1/2\alpha}$ Half-life of distribution phase
$T_{1/2\beta}$ Half-life of elimination phase
$T_{1/2k01}$ Absorption half-life
$T_{lag}$ Lag time
$T_{max}$ Time to maximum observed plasma drug concentration
$T_{Cmax50}$ Time to reach 50% of $C_{max}$
Vz/F Volume of distribution divided by fraction of drug absorbed The features and other details of the invention will now be more particularly described and pointed out in the claims. It will be understood that the particular embodiments of the invention are shown by way of illustration and not as limitations of the invention. The principle features of this invention may be employed in various embodiments without departing from the scope of the invention. As used herein and in the appended claims, the singular forms "a", "an", and "the" include plural referents unless the context clearly dictates otherwise.

In accordance with the invention, a "dose of levodopa", as that term is used herein means a formulation comprising an amount of levodopa in a dosage form suitable for delivery to a patient by inhalation. In one embodiment, a dose of levodopa in accordance with the invention comprises particles containing levodopa. Particles and methods for delivering levodopa to the respiratory system are described, for example, in U.S. Pat. No. 6,514,482 and U.S. Pat. Reissue No. RE43711, the contents of both are incorporated herein by reference in their entirety. The particles are preferably in the form of a dry powder and are characterized by a fine particle fraction (FPF), geometric and aerodynamic dimensions and by other properties, as further described below.

Gravimetric analysis, using Cascade impactors, is a method of measuring the size distribution of airborne particles. The Andersen Cascade Impactor (ACI) is an eight-stage impactor that can separate aerosols into nine distinct fractions based on aerodynamic size. The size cutoffs of each stage are dependent upon the flow rate at which the ACI is operated. Preferably the ACI is calibrated at 60 L/min.

In one embodiment, a two-stage collapsed ACI is used for particle optimization. The two-stage collapsed ACI consists of stages 0, 2 and F of the eight-stage ACI and allows for the collection of two separate powder fractions. At each stage an aerosol stream passes through the nozzles and impinges upon the surface. Particles in the aerosol stream with a large enough inertia will impact upon the plate. Smaller particles that do not have enough inertia to impact on the plate will remain in the aerosol stream and be carried to the next stage.

The ACI is calibrated so that the fraction of powder that is collected on a first stage is referred to as fine particle fraction FPF (5.6). This FPF corresponds to the % of particles that have an aerodynamic diameter of less than 5.6 μm. The fraction of powder that passed the first stage of the ACI and is deposited on the collection filter is referred to as FPF(3.4). This corresponds to the % of particles having an aerodynamic diameter of less than 3.4 μm. The FPF (5.6) fraction has been demonstrated to correlate to the fraction of the powder that is deposited in the lungs of the patient, while the FPF(3.4) has been demonstrated to correlate to the fraction of the powder that reaches the deep lung of a patient.

The FPF of at least 50% of the particles of the invention is less than about 5.6 μm. For example, but not limited to, the FPF of at least 60%, or 70%, or 80%, or 90% of the particles is less than about 5.6 μm.

Another method for measuring the size distribution of airborne particles is the multi-stage liquid impinger (MSLI). The Multi-stage liquid Impinger (MSLI) operates on the same principles as the Anderson Cascade Impactor (ACI), but instead of eight stages there are five in the MSLI. Additionally, instead of each stage consisting of a solid plate, each MSLI stage consists of a methanol-wetted glass frit. The wetted stage is used to prevent bouncing and re-entrainment, which can occur using the ACI. The MSLI is used to provide an indication of the flow rate dependence of the powder. This can be accomplished by operating the MSLI at 30, 60, and 90 L/min and measuring the fraction of the powder collected on stage 1 and the collection filter. If the fractions on each stage remain relatively constant across the different flow rates then the powder is considered to be approaching flow rate independence.

The particles of the invention have a tap density of less than about 0.4 g/cm³. Particles which have a tap density of less than about 0.4 g/cm³ are referred to herein as "aerodynamically light particles". For example, the particles have a tap density less than about 0.3 g/cm³, or a tap density less than about 0.2 g/cm³, a tap density less than about 0.1 g/cm³. Tap density can be measured by using instruments known to those skilled in the art such as the Dual Platform Microprocessor Controlled Tap Density Tester (Vankel, N.C.) or a GEOPYC™ instrument (Micrometrics Instrument Corp., Norcross, Ga. 30093). Tap density is a standard measure of the envelope mass density. Tap density can be determined using the method of USP Bulk Density and Tapped Density, United States Pharmacopia convention, Rockville, Md., 10$^{th}$ Supplement, 4950-4951, 1999. Features which can contribute to low tap density include irregular surface texture and porous structure.

The envelope mass density of an isotropic particle is defined as the mass of the particle divided by the minimum sphere envelope volume within which it can be enclosed. In one embodiment of the invention, the particles have an envelope mass density of less than about 0.4 g/cm$^3$.

The particles in accordance with the invention have a preferred size, e.g., a volume median geometric diameter (VMGD) of at least about 1 micron (μm). In one embodiment, the VMGD is from about 1 μm to 30 μm, or any subrange encompassed by about 1 μm to 30 μm, for example, but not limited to, from about 5 μm to about 30 μm, or from about 10 μm to 30 μm. For example, the particles have a VMGD ranging from about 1 μm to 10 μm, or from about 3 μm to 7 μm, or from about 5 μm to 15 μm or from about 9 μm to about 30 μm. The particles have a median diameter, mass median diameter (MMD), a mass median envelope diameter (MMED) or a mass median geometric diameter (MMGD) of at least 1 μm, for example, 5 μm or near to or greater than about 10 μm. For example, the particles have a MMGD greater than about 1 μm and ranging to about 30 μm, or any subrange encompassed by about 1 μm to 30 μm, for example, but not limited to, from about 5 μm to 30 μm or from about 10 μm to about 30 μm.

The diameter of the spray-dried particles, for example, the VMGD, can be measured using a laser diffraction instrument (for example Helos, manufactured by Sympatec, Princeton, N.J.). Other instruments for measuring particle diameter are well known in the art. The diameter of particles in a sample will range depending upon factors such as particle composition and methods of synthesis. The distribution of size of particles in a sample can be selected to permit optimal deposition to targeted sites within the respiratory tract.

Aerodynamically light particles preferably have "mass median aerodynamic diameter" (MMAD), also referred to herein as "aerodynamic diameter", between about 1 μm and about 5 μm or any subrange encompassed between about 1 μm and about 5 μm. For example, the MMAD is between about 1 μm and about 3 μm, or the MMAD is between about 3 μm and about 5 μm.

Experimentally, aerodynamic diameter can be determined by employing a gravitational settling method, whereby the time for an ensemble of particles to settle a certain distance is used to infer directly the aerodynamic diameter of the particles. An indirect method for measuring the mass median aerodynamic diameter (MMAD) is the multi-stage liquid impinger (MSLI).

The aerodynamic diameter, $d_{aer}$, can be estimated from the equation:

$$d_{aer} = d_g \sqrt{\rho_{tap}}$$

where $d_g$ is the geometric diameter, for example the MMGD, and ρ is the powder density.

Particles which have a tap density less than about 0.4 g/cm$^3$, median diameters of at least about 1 μm, for example, at least about 5 μm, and an aerodynamic diameter of between about 1 μm and about 5 μm, preferably between about 1 μm and about 3 μm, are more capable of escaping inertial and gravitational deposition in the oropharyngeal region, and are targeted to the airways, particularly the deep lung. The use of larger, more porous particles is advantageous since they are able to aerosolize more efficiently than smaller, denser aerosol particles such as those currently used for inhalation therapies.

In comparison to smaller, relatively denser particles the larger aerodynamically light particles, preferably having a median diameter of at least about 5 μm, also can potentially more successfully avoid phagocytic engulfment by alveolar macrophages and clearance from the lungs, due to size exclusion of the particles from the phagocytes' cytosolic space. Phagocytosis of particles by alveolar macrophages diminishes precipitously as particle diameter increases beyond about 3 μm. Kawaguchi, H., et al., *Biomaterials*, 7: 61-66 (1986); Krenis, L. J. and Strauss, B., *Proc. Soc. Exp. Med.*, 107: 748-750 (1961); and Rudt, S. and Muller, R. H., *J. Contr. Rel.*, 22: 263-272 (1992). For particles of statistically isotropic shape, such as spheres with rough surfaces, the particle envelope volume is approximately equivalent to the volume of cytosolic space required within a macrophage for complete particle phagocytosis.

The particles may be fabricated with the appropriate material, surface roughness, diameter and tap density for localized delivery to selected regions of the respiratory tract such as the deep lung or upper or central airways. For example, higher density or larger particles may be used for upper airway delivery, or a mixture of varying sized particles in a sample, provided with the same or different therapeutic agent may be administered to target different regions of the lung in one administration. Particles having an aerodynamic diameter ranging from about 3 to about 5 μm are preferred for delivery to the central and upper airways. Particles having and aerodynamic diameter ranging from about 1 to about 3 μm are preferred for delivery to the deep lung.

Inertial impaction and gravitational settling of aerosols are predominant deposition mechanisms in the airways and acini of the lungs during normal breathing conditions. Edwards, D. A., *J. Aerosol Sci.*, 26: 293-317 (1995). The importance of both deposition mechanisms increases in proportion to the mass of aerosols and not to particle (or envelope) volume. Since the site of aerosol deposition in the lungs is determined by the mass of the aerosol (at least for particles of mean aerodynamic diameter greater than approximately 1 μm), diminishing the tap density by increasing particle surface irregularities and particle porosity permits the delivery of larger particle envelope volumes into the lungs, all other physical parameters being equal.

The low tap density particles have a small aerodynamic diameter in comparison to the actual envelope sphere diameter. The aerodynamic diameter, $d_{aer}$, is related to the envelope sphere diameter, d (Gonda, I., "Physico-chemical principles in aerosol delivery," in *Topics in Pharmaceutical Sciences*, 1991 (eds. D. J. A. Crommelin and K. K. Midha), pp. 95-117, Stuttgart: Medpharm Scientific Publishers, 1992)), by the simplified formula:

$$d_{aer} = d\sqrt{\rho}$$

where the envelope mass density is in units of g/cm$^3$.

Maximal deposition of monodispersed aerosol particles in the alveolar region of the human lung (~60%) occurs for an aerodynamic diameter of approximately $d_{aer}$=3 μm. Heyder, J. et al., *J. Aerosol Sci.*, 17: 811-825 (1986). Due to their small envelope mass density, the actual diameter d of aerodynamically light particles comprising a monodisperse inhaled powder that will exhibit maximum deep-lung deposition is:

$$d = 3/\sqrt{\rho} \text{ μm (where } \rho < 1 \text{ g/cm}^3\text{)};$$

where d is always greater than 3 μm. For example, aerodynamically light particles that display an envelope mass density, μ=0.1 g/cm³, will exhibit a maximum deposition for particles having envelope diameters as large as 9.5 μm. The increased particle size diminishes interparticle adhesion forces. Visser, J., *Powder Technology*, 58: 1-10. Thus, large particle size increases efficiency of aerosolization to the deep lung for particles of low envelope mass density, in addition to contributing to lower phagocytic losses.

The aerodynamic diameter can be calculated to provide for maximum deposition within the lungs. Previously this was achieved by the use of very small particles of less than about five microns in diameter, preferably between about one and about three microns, which are then subject to phagocytosis. Selection of particles which have a larger diameter, but which are sufficiently light (hence the characterization "aerodynamically light"), results in an equivalent delivery to the lungs, but the larger size particles are not phagocytosed. Improved delivery can be obtained by using particles with a rough or uneven surface relative to those with a smooth surface.

In another embodiment of the invention, the particles have an envelope mass density, also referred to herein as "mass density" of less than about 0.4 g/cm³. In some embodiments, the particle density is about 0.01, 0.02, 0.03, 0.04, 0.05, 0.06, 0.07, 0.08, 0.09, less than 0.1, from 0.02 to 0.05, from 0.02 to 0.06 g/cm³. Mass density and the relationship between mass density, mean diameter and aerodynamic diameter are discussed in U.S. Pat. No. 6,254,854, issued on Jul. 3, 2001, to Edwards, et al., which is incorporated herein by reference in its entirety.

Particles that have compositions and aerodynamic properties described above may be produced by several methods including, but not limited to spray drying. Generally, spray-drying techniques are described, for example, by K. Masters in "Spray Drying Handbook", John Wiley & Sons, New York, 1984.

As used herein, the term "effective amount" or "therapeutically effective amount" means the amount needed to achieve the desired effect or efficacy. The actual effective amounts of drug can vary according to the specific drug or combination thereof being utilized, the particular composition formulated, the mode of administration, and the age, weight, condition of the patient, and severity of the episode being treated. In the case of a dopamine precursor, agonist or combination thereof it is an amount which reduces the Parkinson's symptoms which require therapy. Dosages for a particular patient are described herein and can be determined by one of ordinary skill in the art using conventional considerations, (e.g., by means of an appropriate, conventional pharmacological protocol).

Administration of particles to the respiratory system can be by means such as known in the art. For example, particles are delivered from an inhalation device such as a dry powder inhaler (DPI). Metered-dose-inhalers (MDI), nebulizers or instillation techniques also can be employed.

In one embodiment delivery to the pulmonary system of particles is by the methods described in U.S. Pat. No. 6,858, 199 entitled, "High Efficient Delivery of a Large Therapeutic Mass Aerosol", and U.S. Pat. No. 7,556,798, "Highly Efficient Delivery of a Large Therapeutic Mass Aerosol". The entire contents of both these patents are incorporated herein by reference. As disclosed therein, particles are held, contained, stored or enclosed in a receptacle. The receptacle, e.g. capsule or blister, has a volume of at least about 0.37 cm³ and can have a design suitable for use in a dry powder inhaler. Larger receptacles having a volume of at least about 0.48 cm³, 0.67 cm³ or 0.95 cm³ also can be employed. As used herein, the term "receptacle" includes but is not limited to, for example, a capsule, blister, film covered container well, chamber and other suitable means of storing particles, a powder or a respirable composition in an inhalation device known to those skilled in the art. In one embodiment, the receptacles are capsules, for example, capsules designated with a particular capsule size, such as 2, 1, 0, 00 or 000. Suitable capsules can be obtained, for example, from Shionogi (Rockville, Md.). In one embodiment, the capsule shell may comprise hydroxypropyl methylcellulose (HPMC). In a further embodiment, the capsule shell may comprise hydroxypropyl methylcellulose (HPMC) and titanium dioxide. Blisters can be obtained, for example, from Hueck Foils, (Wall, N.J.). Other receptacles and other volumes thereof suitable for use in the instant invention are known to those skilled in the art.

In one embodiment, the invention provides administering L-Dopa to the pulmonary system in a small number of steps, and preferably in a single, breath activated step. In one embodiment, at least 50%, preferably at least 60% and preferably at least 70% of the mass of particles stored in the inhaler receptacle is delivered to a subject's respiratory system in a single, breath-activated step. In one embodiment, at least 80% of the mass of the particles stored in the inhaler receptacle is delivered to a subject's respiratory system in a single, breath-activated step. In another embodiment, at least 1 to 80 milligrams of L-Dopa is delivered by administering, in a single breath, to a subject's respiratory tract particles enclosed in the receptacle. Preferably at least 10 15, 20, 25, 30, 35, 40, 50, 60, 75 and 80 milligrams can also preferably be delivered.

Delivery to the pulmonary system of particles in a single, breath-actuated step is enhanced by employing particles which are dispersed at relatively low energies, such as, for example, at energies typically supplied by a subject's inhalation. Such energies are referred to herein as "low." As used herein, "low energy administration" refers to administration wherein the energy applied to disperse and/or inhale the particles is in the range typically supplied by a subject during inhaling.

The invention also is related to methods for efficiently delivering powder particles to the pulmonary system. For example, but not limited to, at least about 60%, preferably at least about 70%, or more preferably at least about 80% of the nominal powder dose is actually delivered.

In one embodiment, compositions used in this invention comprise particles such as dry powder particles suitable for pulmonary delivery comprising about 60-99% by weight (dry weight) of levodopa. Particularly preferred are particles that include about 75% by weight or more of levodopa and even more preferably comprise about 90% by weight or more of levodopa. Particles can consist entirely of L-Dopa or can further include one or more additional components. Examples of such suitable additional components include, but are not limited to, phospholipids, amino acids, sugars and salts. Specific examples of phospholipids include but are not limited to phosphatidylcholines dipalmitoyl phosphatidylcholine (DPPC), dipalmitoyl phosphatidylethanolamine (DPPE), distearoyl phosphatidylcholine (DSPC), dipalmitoyl phosphatidyl glycerol (DPPG) or any combination thereof. The amount of phospholipids, e.g., DPPC, present in the particles of the invention generally is less than 10 wt %.

Salts include a small amount of a strong electrolyte salt, such as, but not limited to, sodium chloride (NaCl). Other salts that can be employed include sodium citrate, sodium lactate, sodium phosphate, sodium fluoride, sodium sulfate and calcium carbonate. Generally, the amount of salt present in the particles is less than 10 wt %, for example, less than 5 wt %.

In one preferred embodiment, a formulation of levodopa suitable for pulmonary delivery to a patient by inhalation comprises, 90% by weight of levodopa, 8% by weight of dipalmitoyl phosphatidylcholine (DPPC) and 2% by weight sodium chloride and is referred to herein as "90/8/2".

In one embodiment dosing regimens of levodopa administered by inhalation at doses of 10 to 50 mg levodopa fine particle dose (FPD) provide rapidly increasing, dose-proportional plasma levodopa concentrations, achieving therapeutically relevant levels within 5 to 10 minutes after fine particle doses ranging from 10 to 50 mg FPD and preferably from 20 to 50 mg FPD. Surprisingly, it was discovered that between-subject variability in plasma concentrations following treatment was much less following levodopa inhalation than following oral administration. It was also unexpected that between-subject variability would be reduced by pulmonary administration of levodopa.

Therefore, in one embodiment the interpatient variability of the levodopa plasma concentration at any time period from about 10 minutes post inhalation to about 60 minutes post inhalation has a coefficient of variation that is less than from about 50% to about 5%. In one embodiment the interpatient variability of the levodopa plasma concentration at any time period from about 10 minutes post inhalation to about 60 minutes post inhalation has a coefficient of variation that is less than from about 50% to about 10%. In one embodiment the interpatient variability of the levodopa plasma concentration at any time period from about 10 minutes post inhalation to about 60 minutes post inhalation has a coefficient of variation that is less than from about 35% to about 10%. In one embodiment the interpatient variability of the levodopa plasma concentration at any time period from about 30 minutes post inhalation to about 60 minutes post inhalation has a coefficient of variation that is less than from about 35% to about 10%.

In one embodiment the interpatient variability of the levodopa plasma concentration at any time period from about 10 minutes post inhalation, preferably about 15 minutes post inhalation, preferably about 20 minutes post inhalation, preferably about 30 minutes post inhalation, and more preferably about 60 minutes post inhalation, has less than a 50% coefficient of variation, preferably less than a 45% coefficient of variation, preferably less than a 40% coefficient of variation, preferably less than a 35% coefficient of variation, preferably less than a 30% coefficient of variation, preferably less than a 25% coefficient of variation, preferably less than a 20% coefficient of variation, preferably less than a 15% coefficient of variation and preferably less than a 10% coefficient of variation preferably less than a 5% coefficient of variation. In one embodiment the interpatient variability at the time period of 10 minutes post inhalation, preferably about 30 minutes post inhalation, and more preferably about 60 minutes post inhalation, has less than a 35% coefficient of variation.

In one embodiment the patient is a Parkinson's patient suffering from altered gastric motility. In one embodiment the patient is a stage 2, 3, or 4 Parkinson's patient. In one embodiment, the dosage given by inhalation provides a higher plasma concentration at 10 minutes as compared to an equivalent dose of levodopa given orally. In one embodiment, the patient does not require a dose titration of levodopa. In one embodiment, the patient is suffering from motor fluctuations that are not relieved by oral medications for treating Parkinson's disease.

In one embodiment, the interpatient variability of the levodopa AUC at the time period of about 10 minutes post inhalation, preferably about 30 minutes post inhalation, and more preferably about 60 minutes post inhalation, has less than a 50% coefficient of variation. In one embodiment the interpatient variability at the time period of 10 minutes post inhalation, preferably about 30 minutes post inhalation, and more preferably about 60 minutes post inhalation, has less than a 35% coefficient of variation. In one embodiment the patient is a Parkinson's patient suffering from altered gastric motility. In one embodiment the patient is a stage 2, 3, or 4 Parkinson's patient. In one embodiment, the dosage given by inhalation provides a higher AUC at 10 minutes as compared to an equivalent dose of levodopa given orally. In one embodiment, the patient does not require a dose titration of levodopa. In one embodiment, the patient is suffering from motor fluctuations that are not relieved by oral medications for treating Parkinson's disease.

In one preferred embodiment the dose of levodopa used in any of the methods of the inventions comprises 90% by weight levodopa, 8% by weight dipalmitoylphosphatidylcholine (DPPC) and 2% by weight of sodium chloride.

The administration of more than one dopamine precursor, DOPA decarboxylase inhibitor or combinations thereof, including, but not limited to, L-Dopa, carbidopa, apomorphine and benserazide can be provided, either simultaneously or sequentially in time to administration of levodopa by inhalation in accordance with the invention. In one embodiment the administration of more than one dopamine precursor or DOPA decarboxylase inhibitor can be administered by intramuscular, subcutaneous, oral and other administration routes. In one embodiment, these other agents are also co-administered via the pulmonary system. These compounds or compositions can be administered before, after or at the same time as pulmonary administration of levodopa by inhalation and are deemed to be "co-administered" when used in conjunction with administration of levodopa via inhalation in accordance with the methods described herein.

In one embodiment, the patient does not require the co-administration of a DOPA decarboxylase inhibitor or allows for a lower or less frequent dose of a DOPA decarboxylase inhibitor. In another embodiment, the patient does not require the co-administration of carbidopa or allows for a lower or less frequent dose of carbidopa as compared to a patient receiving L-Dopa orally. In a further embodiment, the patient does not require the co-administration of benserazide or allows for a lower or less frequent dose of benserazide as compared to a patient receiving L-Dopa orally.

In one embodiment, the invention comprises a method of reducing the inter-patient variability of levodopa in a patient population of Parkinson's disease patients comprising administering levodopa by inhalation to a patient population of at least two patients suffering from Parkinson's disease; wherein the inter-patient variability of the levodopa plasma concentration at the time period of ten minutes post inhalation has less than a 50% coefficient of variation and wherein said patient is not administered a DOPA decarboxylase inhibitor.

The following Examples are intended to illustrate the invention but cannot be construed as limiting the scope thereof.

Example 1

Summary

A 90/8/2 dry powder levodopa formulation was provided to evaluate the safety, tolerability and levodopa pharmacokinetics (PK) following administration of 90/8/2 pulmonary levodopa powder compared with oral levodopa in adult healthy volunteers. The pulmonary levodopa powder described in these examples is comprised of particles of 90% levodopa, 8% dipalmitoylphosphatidylcholine and 2% sodium chloride, all by dry weight and is referred to herein as "90/8/2." This data provides a description of the PK of levodopa following single inhaled doses of 90/8/2 and a comparison to orally administered levodopa (LD) in the fasted or fed conditions as well as a comparison of the PK with and without pretreatment with carbidopa (CD). This was a two-part study in healthy adult male and female subjects as follows: Part A-Dose Escalation Segment with comparison to oral levodopa; and Part B-90/8/2 plus or minus a Carbidopa Pre-treatment Segment.

Part A was an open-label, 3-period crossover, single-ascending dose study. Each subject received a single oral dose of CD/LD (25/100 mg) in a fed or fasted state in one session, and two different doses of inhaled 90/8/2 (10 and 30 mg or 20 and 50 mg levodopa fine particle dose (FPD)), in single ascending doses, in two different treatment sessions. Two groups of nine subjects each were enrolled.

Part B was an open-label, randomized, two-period, period balanced crossover study. Eight subjects underwent an evaluation of the safety, tolerability and levodopa PK following administration of a single inhaled 90/8/2 dose (40 mg levodopa FPD) with and without pre-treatment with CD.

Blood samples were collected over 24 hours and plasma levodopa concentrations were determined by Simbec Research Limited (UK) using a validated liquid chromatography-tandem mass spectrometry (LC-MS-MS) assay with a lower limit of quantitation of 9.84 ng/mL. Pharmacokinetic analysis was performed using non-compartmental methods followed by PK modeling using a two-compartment model with a lag time. 90/8/2 administered by inhalation at doses of 10 to 50 mg levodopa FPD produced rapidly increasing, dose-proportional plasma levodopa concentrations, achieving potentially therapeutically relevant levels within 5 to 10 minutes after fine particle doses of 20 to 50 mg in healthy adults.

Levodopa plasma concentrations following 90/8/2 inhalation increased faster than those following oral administration in the fasted condition and much faster than those under fed conditions. Exposure over the first ten minutes following drug administration expressed as the partial area under the plasma concentration versus time curve, AUC from 0 to 10 minutes ($AUC_{0-10m}$) and as the maximum plasma concentration observed over the first ten minutes post-dose ($C_{max,10m}$) indicated much earlier systemic exposure following 90/8/2 inhalation compared to oral administration.

Subject to subject variability in plasma concentrations was greatly reduced with inhalation compared to oral administration and what would have been expected with pulmonary administration. The analysis also indicated that oral administration in the fasted state lead to more rapid absorption compared to the fed state but still much slower than following inhalation. Pharmacokinetic modeling indicated a lag time of approximately 9 to 10 minutes following oral administration in the fed or fasted state compared to a lag time of less than 0.5 minute following 90/8/2 inhalation. Furthermore, the absorption half-life was shorter following inhalation compared to oral administration.

Following 90/8/2 inhalation, systemic levodopa exposure was proportional to the 90/8/2 dose administered. Dose-normalized $C_{max}$ and AUC were very similar across the 90/8/2 doses administered. Dose-normalized (based on estimated fine particle dose) exposure following inhalation was 1.3 to 1.6 times greater based on AUC and 1.6 to 2.9 times greater based on $C_{max}$ compared to oral administration. As has been described in the literature, following oral administration, considerable reduction in $C_{max}$ and prolongation in $T_{max}$ was observed in fed subjects; however, AUC was similar between fed and fasted subjects.

Plasma concentrations from Part B of the study in which a 40 mg fine particle dose of 90/8/2 was inhaled with or without carbidopa pretreatment in a cross-over design demonstrated rapid absorption with plasma concentration achieving potentially therapeutic levels. Plasma levodopa clearance was approximately four-fold faster without CD pretreatment. Correspondingly, $C_{max}$ and AUC were lower and $T_{max}$ and $T_{1/2}$ were somewhat shorter without CD pretreatment. The main findings of this study were:

- Inhaled 90/8/2 resulted in rapid increases in plasma levodopa concentrations;
- Systemic exposure to levodopa based on $C_{max}$ and AUC was much greater over the first 10 minutes after dosing with 90/8/2 inhalation compared to oral drug administration;
- Potentially therapeutically relevant levodopa plasma concentrations were achieved within 5 to 10 minutes after inhalation of fine particle doses of 20 to 50 mg in healthy adults;
- Subject to subject variability in plasma levodopa concentrations was considerably less following inhalation compared to oral administration and what would have been expected with pulmonary administration;
- Systemic levodopa exposure was proportional to levodopa fine particle dose administered;
- Pharmacokinetic modeling indicated that inhaled 90/8/2 had much shorter lag times and faster absorption rates than oral administration;
- Dose-normalized (based on estimated fine particle dose) exposure following inhalation was 1.3 to 1.6 times greater based on AUC and 1.6 to 2.9 times greater based on $C_{max}$ compared to oral administration;
- Plasma levodopa clearance was approximately four-fold greater and levodopa exposure was reduced in the absence of carbidopa pre-treatment.

Introduction

In this example, 90/8/2 is being tested as an episodic treatment of motor fluctuations ("off episodes") in patients with Parkinson's disease who experience intermittent inadequate response to their standard oral medications. 90/8/2 may be used as an adjunct to the patient's existing dopadecarboxylase inhibitor (i.e., carbidopa or benserazide)-inclusive Parkinson's disease medication regimen. This study is the first study in humans with 90/8/2 and is designed to evaluate the safety, tolerability and levodopa pharmacokinetics (PK) following administration of 90/8/2 compared with oral levodopa in adult healthy volunteers.

Safety and tolerability results have been tested in clinical trials. This PK data analysis provides a description of the PK of levodopa following single inhaled doses of 90/8/2 and a comparison to orally administered levodopa (LD; L-Dopa) in the fasted or fed conditions as well as a comparison of the PK of levodopa with and without pretreatment with carbidopa (CD). Oral levodopa was administered as a routinely prescribed combined carbidopa/levodopa preparation.

Study Design and Objectives

This was a two-part study in healthy adult male and female subjects as follows:

Part A: Dose Escalation Segment with comparison to oral levodopa

Part B: 90/8/2±Carbidopa Pre-treatment Segment

The primary pharmacokinetic objective of Part A of the study was to investigate the pharmacokinetics of levodopa following administration of single, inhaled doses of 90/8/2 in healthy adults. Secondary objectives were to explore the dose proportionality of levodopa following single inhaled dose administration and to compare the PK of 90/8/2 to oral levodopa administered in the fasted state or fed state. The objective of Part B was to compare the tolerability and pharmacokinetics of 90/8/2 with and without pretreatment with carbidopa.

Part A was an open-label, 3-period crossover, single-ascending dose study. All subjects were treated with oral carbidopa one day prior to and on the day of study drug treatment. Each subject received a single oral dose of CD/LD (25/100 mg) in a fed or fasted state in one session, and two different inhaled doses of 90/8/2, in single ascending doses, in two different sessions. Two groups of nine subjects each were enrolled. The study design for Part A is outlined in Table 1 below:

TABLE 1

Part A Study Design.

| Group | N | Dose Group | Levodopa Dose* (mg) |
|---|---|---|---|
| 1 | 9 | Oral CD/LD Fed or Fasted | 100 |
|   |   | 90/8/2 Dose Level 1 | 10 |
|   |   | 90/8/2 Dose Level 3 | 30 |
| 2 | 9 | Oral CD/LD Fed or Fasted | 100 |
|   |   | 90/8/2 Dose Level 2 | 20 |
|   |   | 90/8/2 Dose Level 4 | 50. |

*Levodopa dose for 90/8/2 administration indicates estimated fine particle dose (FPD; i.e., 'lung-delivered' dose); oral CD/LD (25 mg/100 mg).

Part B was an open-label, two-period, period balanced crossover study. Following preliminary review of safety and PK data from Part A, eight subjects underwent an evaluation of the safety, tolerability and levodopa PK following administration of a single inhaled 90/8/2 dose (40 mg levodopa FPD) with and without pre-treatment with CD in a randomized, balanced fashion so that equal numbers of subjects received one of the two dosing sequences A→B or B→A, defined as follows:

Regimen A: 90/8/2 with CD pre-treatment
Regimen B: 90/8/2 without CD pre-treatment Carbidopa treatments in Parts A and B of the study were standardized according to the schedule in Table 2.

In Part A, blood samples were collected pre-dose and following oral CD/LD administration at 10, 20, 30, 45, 60, 75, 90, 120 min, 4, 8, 16 and 24 h. During 90/8/2 inhalation treatment sessions in Parts A and B, samples were collected at the same times plus additional samples at 1, 2, and 5 minutes. Plasma levodopa concentrations were determined by Simbec Research Limited using a validated liquid chromatography-tandem mass spectrometry (LC-MS-MS) assay with a lower limit of quantitation of 9.84 ng/mL (2, 3).

TABLE 2

Carbidopa Treatment Schedule.

| | Carbidopa (LODOSYN ®) Dose and Timing | |
|---|---|---|
| Treatment Session | Day −1 | Day 1* |
| Oral CD/LD: Part A | 50 mg every 8 h prior to Day 1 dosing (0, 8 and 16 h, ≥1 h from the nearest meal)** | 25 mg*** 1 h pre-dose 50 mg 7 and 15 h post-dose |
| 90/8/2: Part A & | 50 mg every 8 h prior to Day 1 | 50 mg 1 h pre-dose, |

TABLE 2-continued

Carbidopa Treatment Schedule.

| | Carbidopa (LODOSYN ®) Dose and Timing | |
|---|---|---|
| Treatment Session | Day −1 | Day 1* |
| Part B (+CD) | dosing (0, 8 and 16 h, ≥1 h from the nearest meal) | 7 and 15 h post-dose |
| 90/8/2: Part B (−CD) | — | 50 mg 7 and 15 h post-dose. |

*When an oral and inhaled dosing session were scheduled to occur over two consecutive days, the CD dosing regimen administered for the first dosing session adequately covered the CD pre-treatment required for the second dosing session. Subjects in Part A and Part B (+CD) received 3 doses of CD during the day before receipt of study medication.
**Does not apply to subjects randomized to fed state.
***Note:
25 mg carbidopa also administered at T0 as part of oral CD/LD administration Pharmacokinetic Analysis Methods Non-Compartmental Analysis Data analysis was performed on plasma concentrations and time for each subject and each treatment. Non-compartmental analysis was performed with WINNONLIN® professional version 5.3. The area under the curve from time zero to the last measurable time point ($AUC_{0-t}$) was estimated using the linear trapezoid method. Linear regression over the last three or more time points was used to estimate the elimination rate constant ($\lambda$) which was used to estimate terminal half-life ($T_{1/2}$) and AUC from zero to infinity ($AUC_{0-\infty}$) from the following equations:

$$T_{1/2}=\ln(2)/\lambda$$

$$AUC_{0-\infty}=AUC_{0-t}+C_t/\lambda$$

where $C_t$ is the last measurable concentration predicted by the regression line. Serum clearance divided by bioavailability (CL/F) and the apparent volume of distribution in the terminal phase divided by the bioavailability (Vz/F) were estimated from the equations below:

$$CL/F=Dose/AUC_{0-\infty}$$

$$Vz/F=Dose/(\lambda * AUC_{0-\infty})$$

The maximum concentration ($C_{max}$) and the time it was observed ($T_{max}$) were determined directly from the data.

The partial AUC over the first 10 minutes after drug administration ($AUC_{0-10m}$) was calculated by the trapezoid method. The maximum plasma concentration observed over the first 10 minutes ($C_{max, 10m}$) was determined as the highest plasma concentration observed from dosing up to an including the 10 minute sampling time Inhalation-to-oral exposure ratios were calculated for each subject by dividing the dose-normalized $C_{max}$ or AUC following 90/8/2 inhalation by the dose-normalized parameter following oral administration. The exposure ratio based on AUC is the relative bioavailability of inhaled to oral drug.

An additional parameter, time to achieve half of the maximum observed plasma concentration, ($T_{Cmax50}$) was calculated (MICROSOFT® EXCEL®) by linear interpolation between the two time points with the plasma concentrations bracketing the plasma concentration calculated from $C_{max}$ divided by two.

Pharmacokinetic Modeling

Pharmacokinetic modeling was performed using WINNONLIN®, professional version 5.3. A number of different models were evaluated including one- and two-compartment models with and without lag times. All evaluated models had first order input. Models were evaluated based on a number of diagnostic criteria including the Aikaike Information Criterion, the sum of squared residuals, the relative values of the estimated parameters and their respective standard error estimates, the correlation of observed and predicted concentrations, and general trends in variation between predicted and observed concentrations.

Figure 8:
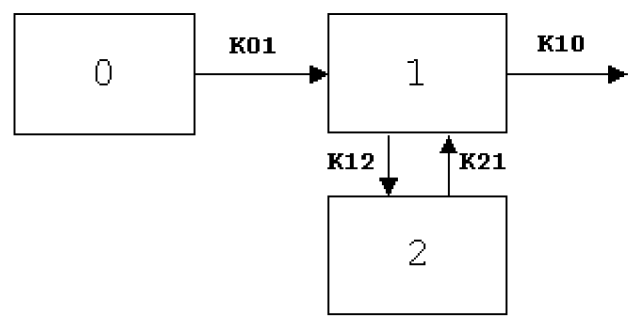
FIG. 8. Scheme of modeling using a two-compartment model.

The model that best described most of the plasma concentration versus time curves was a two-compartment model with a lag time (WINNONLIN® model 12). Most of the data sets from subjects receiving inhaled 90/8/2 were also well described by a model without a lag time because the estimated lag times from these subjects were very short, less than one minute in most cases. However for comparison to data sets from oral administrations the lag time model was used for all subjects and all treatments. Most data sets were described better by a two-compartment model than a one-compartment model. In some cases a one-compartment model could not be fit. For cases in which a one-compartment model was better, based on the statistical diagnostic criteria, the difference between the two models was very small. Therefore, the results of modeling using a two-compartment model are presented herein. The two-compartment model shown in FIG. 8, generates estimates for the volume of distribution divided by the fraction of dose absorbed (V/F), the lag time ($T_{lag}$), the rate constants associated with absorption and elimination, k01 and k10, respectively, and the inter-compartmental rate constants, k12 and k21. The rate constants associated with the distribution and elimination phases of the curve, α and β, are calculated from k12, k21, and k10. Other secondary parameters calculated from the primary parameters include AUC, $C_{max}$, $T_{max}$, CL/F, and the half-lives associated with the absorption, distribution and elimination phases of the curve ($T_{1/2k01}$, $T_{1/2\alpha}$, $T_{1/2\beta}$). The model is represented by the equation:

$$C_t = Ae^{-\alpha t} + Be^{-\beta t} + Ce^{-k01 t}$$

$C_t$ is the plasma levodopa concentration at time t after administration, A, B and C are the y-axis intercepts of the distribution, elimination and absorption phases of the curve and are calculated from the dose, volume and rate constants.

Uniform weighting was used in all analyses and plasma concentrations reported as below the level of quantitation of the assay (BLQ, <9.84 ng/mL) were treated as missing values. No data points were excluded from the analyses.

Results and Discussion

90/8/2 administered by inhalation at doses of 10 to 50 mg levodopa FPD produced rapidly increasing, dose-proportional plasma levodopa concentrations, achieving potentially therapeutically relevant levels (400 to 500 ng/mL) within 5 to 10 minutes after fine particle doses of 20 to 50 mg levodopa in healthy adults.

FIG. 1 presents the mean levodopa plasma levodopa concentrations following 90/8/2 inhalation and following a 100 mg oral dose under fed and fasted conditions. Individual values and concentration versus time plots were calculated for each inhaled dosage of 10 mg, 20 mg, 30 mg and 50 mg levodopa, respectively as well as 100 mg levodopa orally under fed and fasted conditions and with and without carbidopa pretreatment.

Figure 3:
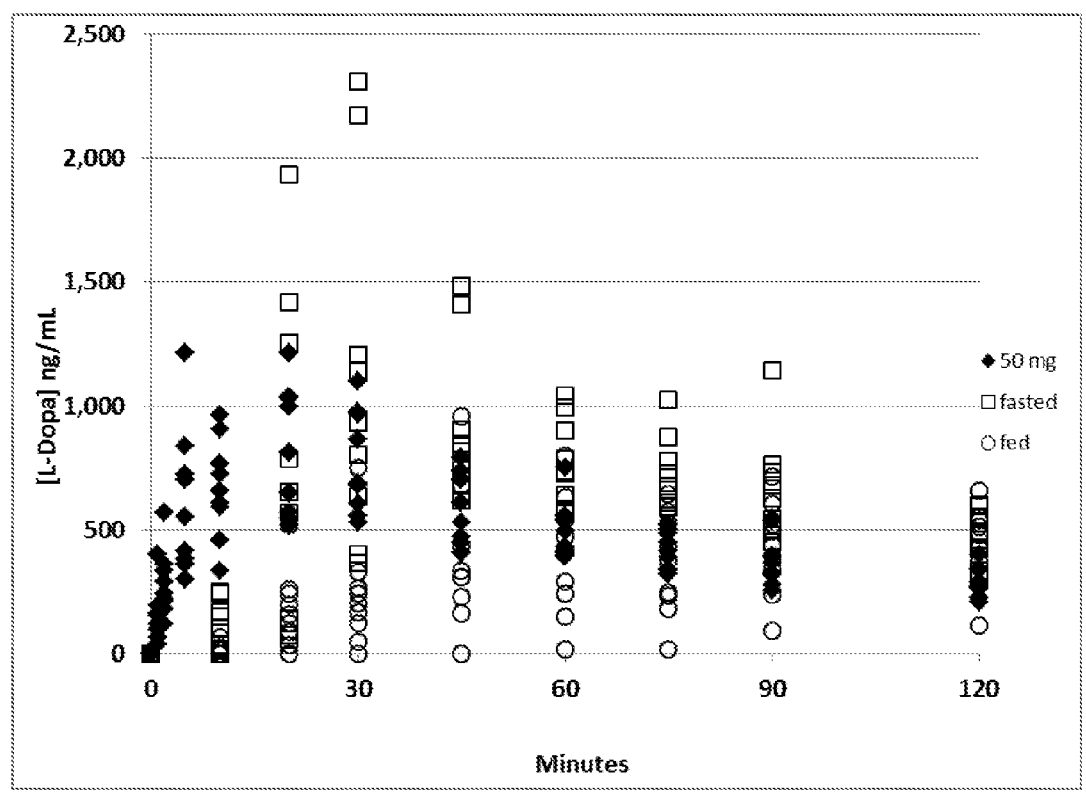
FIG. 3: Plasma levodopa concentrations in individual subjects following inhalation of 50 mg 90/8/2 or oral administration of 100 mg levodopa (CD/LD 25/100 mg) under fed and fasted conditions.

Plasma levodopa concentrations following 90/8/2 inhalation increased faster than those following oral administration in the fasted condition and much faster than those under fed conditions. Potentially therapeutically relevant plasma concentrations were achieved by approximately five minutes following 90/8/2 inhalation. Within five minutes of inhalation of 90/8/2, 20 to 50 mg FPD, plasma concentrations were 400 to 500 ng/mL or greater, a range that has been observed to be of potential therapeutic relevance (4). Plasma concentrations achieved following 90/8/2, 40 and 50 mg FPD were in the same range as those observed following oral CD/LD (25/100 mg) dosing (FIG. 3).

Figure 2:
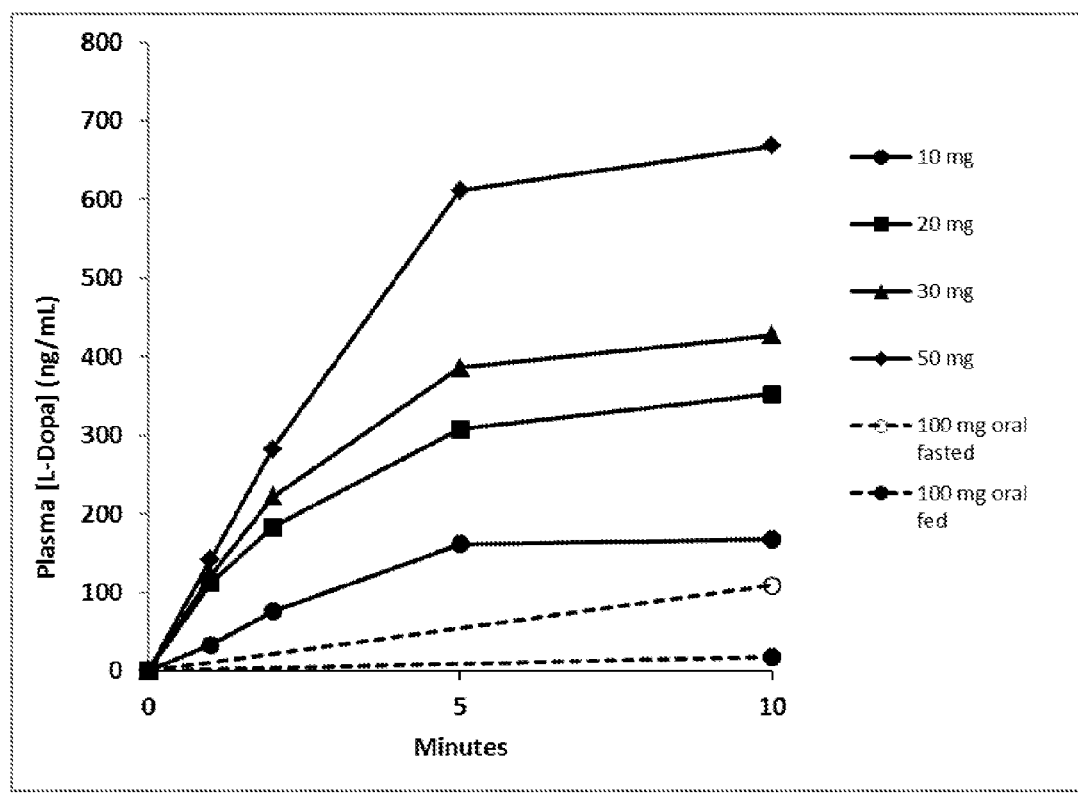
FIG. 2: Mean plasma levodopa concentration vs. time data following 90/8/2 inhalation compared to oral administration.

FIG. 2 shows the mean plasma concentrations over the first ten minutes compared to those following oral administration. Exposure over the first ten minutes following drug administration is expressed both as the AUC from 0 to 10 minutes ($AUC_{0-10m}$) and as the maximum plasma concentration observed over the first ten minutes ($C_{max,10m}$) in Table 3. In some individuals the $C_{max,10m}$ was observed in less than 10 minutes.

Oral administration in the fasted state lead to more rapid absorption compared to the fed state but still much slower than following inhalation. As has been described in the literature (5), following oral administration, considerable reduction in $C_{max}$ and prolongation in $T_{max}$ was observed in fed subjects; however, AUC (Table 5) was similar between fed and fasted subjects.

TABLE 3

Levodopa Exposure after 90/8/2 Inhalation or Oral Levodopa Administration.

| Dose (mg) | Mean ± SD $C_{max, 10m}$ (ng/mL) | Mean ± SD $AUC_{0-10m}$ (ng-min/mL) | Median $T_{Cmax50}$ min | Median $T_{max}$ min |
|---|---|---|---|---|
| 90/8/2 | | | | |
| 10 | 187 ± 58 | 1240 ± 391 | 3.08 | 10 |
| 20 | 368 ± 148 | 2590 ± 1283 | 2.64 | 10 |
| 30 | 456 ± 59 | 3176 ± 769 | 2.90 | 30 |
| 50 | 729 ± 265 | 4824 ± 1896 | 4.10 | 20 |
| Oral | | | | |
| 100 Oral fasted | 109 ± 99 | 561 ± 477 | 18.32 | 45 |
| 100 Oral fed | 18 ± 21 | 124 ± 95 | 39.84 | 120. |

Between-subject variability in plasma concentrations following treatment was much less following 90/8/2 inhalation than following oral administration. As seen in FIG. 3, following inhalation (filled symbols), plasma concentrations in most subjects receiving 50 mg 90/8/2 were above 400 ng/mL at 10 minutes after dosing, some were above 400 ng/mL at 5 minutes, and all by 20 minutes. Following oral administration (open symbols), the response was much slower with no subjects approaching 400 ng/mL within 10 minutes of dosing. Individual plasma concentration and variability data for other dose groups, indicate that at levodopa FPD doses of 20 mg and above plasma concentrations above 400 ng/mL were achieved in some subjects within 5 to 10 minutes of dosing and the responses were much less variable than following oral administration. The extent of variability expressed as the % CV in plasma concentrations within a treatment group at a given sampling time, shown in Table 4, demonstrates that within the first 30 minutes of dosing the variability in the 90/8/2 treated subjects was less than half that seen in the fasted oral group and approximately five-fold less than all oral subjects (fed and fasted combined).

TABLE 4

Variability in Plasma Levodopa Concentrations (% CV).

| | Minutes after Dosing | | | | | | | |
|---|---|---|---|---|---|---|---|---|
| | 10 | 20 | 30 | 45 | 60 | 75 | 90 | 120 |
| 90/8/2* | | | | | | | | |
| 10 mg | 31 | 43 | 42 | 29 | 28 | 25 | 26 | 20 |
| 20 mg | 43 | 39 | 35 | 26 | 27 | 31 | 35 | 24 |

TABLE 4-continued

Variability in Plasma Levodopa Concentrations (% CV).

| | Minutes after Dosing | | | | | | | |
|---|---|---|---|---|---|---|---|---|
| | 10 | 20 | 30 | 45 | 60 | 75 | 90 | 120 |
| 30 mg | 18 | 19 | 21 | 18 | 24 | 15 | 12 | 10 |
| 50 mg | 30 | 32 | 27 | 23 | 24 | 18 | 30 | 23 |
| Oral** | | | | | | | | |
| Oral (fasted) | 91 | 86 | 64 | 34 | 22 | 20 | 32 | 22 |
| Oral (all) | 132 | 117 | 101 | 62 | 48 | 47 | 42 | 27 |

*Refers to estimated levodopa fine particle dose
**Oral levodopa dose 100 mg

Figure 4:
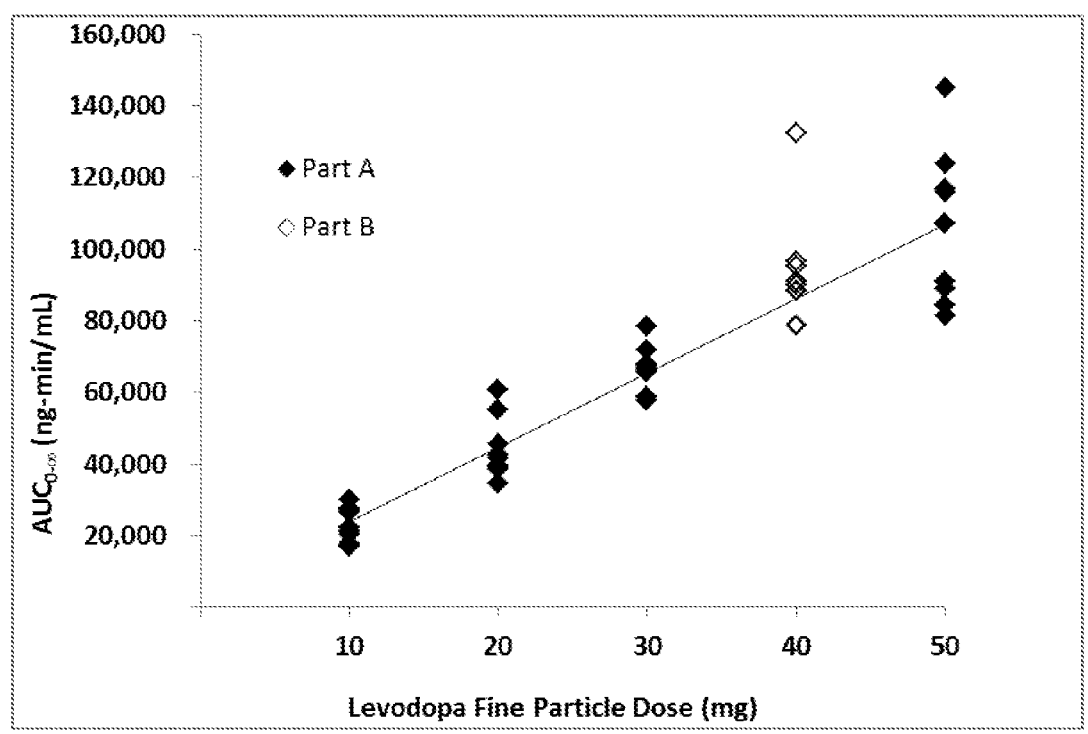
FIG. 4: Levodopa $AUC_{0-\infty}$ vs 90/8/2 fine particle dose.
Figure 5:
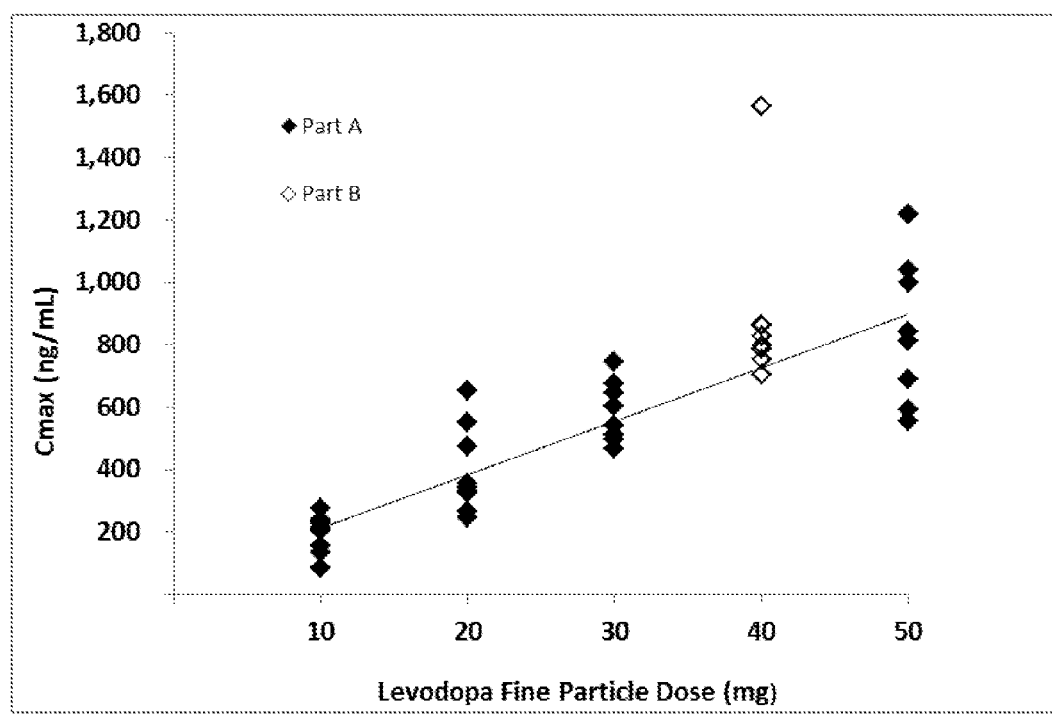
FIG. 5: Levodopa $C_{max}$ vs 90/8/2 fine particle dose.

A summary of the pharmacokinetic parameters estimated by non-compartmental analysis is shown in Table 5. Parameter estimates for individuals were determined from the non-compartmental PK analyses for each inhaled dosage of 10 mg, 20 mg, 30 mg and 50 mg as well as 100 mg oral dosage under fasted and fed conditions and with and without CD pretreatment. The results indicate that levodopa exposure was proportional to the 90/8/2 dose administered. Dose-normalized $C_{max}$ and AUC are very similar for all 90/8/2 doses. Dose proportionality is further illustrated in FIG. 4 and FIG. 5. $T_{1/2}$ is similar for all doses.

TABLE 5

Levodopa Pharmacokinetic Parameters (Mean ± SD) Estimated by Non-compartmental Analysis.

| Dose mg* | $C_{max}$ ng/mL | $C_{max/Dose}$ ng/mL/mg | AUC ng-min/mL | AUC/Dose ng-min/mL/mg | $T_{1/2}$*** min |
|---|---|---|---|---|---|
| 90/8/2** | | | | | |
| 10 | 196 ± 60 | 19.60 ± 5.99 | 23,374 ± 4,656 | 2,337 ± 466 | 120 |
| 20 | 393 ± 137 | 19.67 ± 6.83 | 44,150 ± 8,504 | 2,208 ± 425 | 122 |
| 30 | 576 ± 95 | 19.19 ± 3.17 | 66,914 ± 6,185 | 2,230 ± 206 | 108 |
| 50 | 884 ± 249 | 17.69 ± 4.99 | 106,011 ± 21,234 | 2,120 ± 427 | 101 |
| Oral | | | | | |
| 100(fasted) | 1,317 ± 558 | 13.17 ± 5.58 | 156,598 ± 26,921 | 1,566 ± 269 | 101 |
| 100(fed) | 637 ± 144 | 6.37 ± 1.44 | 159,042 ± 30,544 | 1,590 ± 305 | 114 |

*Dose: levodopa dose
**Refers to estimated fine particle dose
***Median value

Bioavailability of inhaled 90/8/2 relative to oral levodopa was calculated for individual subjects from the ratios of the dose-normalized $AUC_{0-\infty}$. Since each subject in Part A of the study received one oral and two inhaled doses, two bioavailability estimates were determined for each subject, one for each inhaled dose. Relative exposure calculations were also performed on the dose-normalized $C_{max}$ values. Calculations were performed separately for oral doses administered under fed and fasted conditions. The means and standard deviations for the relative bioavailability calculations are presented in Table 6. Individual values were calculated as relative levodopa exposures following inhalation of 90/8/2 (10-50 mg levodopa fine particle dose) compared to carbidopa/levodopa 25/100 mg) oral administration calculated from the dose-normalized Cmax. There does not appear to be a major difference between fed and fasted subjects or among dose groups. Dose-normalized (based on estimated fine particle dose) exposure following inhalation was approximately 1.3 to 1.6 times greater based on AUC and 1.6 to 2.9 times greater based on $C_{max}$ compared to oral administration.

TABLE 6

Exposure Ratios (Mean ± SD) of Inhaled 90/8/2 Relative to Oral Levodopa

| 90/8/2 | AUC | | $C_{max}$ | |
|---|---|---|---|---|
| FPD mg | Oral Fasted | Oral Fed | Oral Fasted | Oral Fed |
| 10 | 1.61 ± 0.27 | 1.31 ± 0.37 | 1.72 ± 0.72 | 2.95 ± 1.47 |
| 20 | 1.50 ± 0.12 | 1.41 ± 0.23 | 1.96 ± 0.60 | 2.81 ± 1.04 |
| 30 | 1.47 ± 0.11 | 1.34 ± 0.34 | 1.65 ± 0.63 | 2.89 ± 0.29 |
| 50 | 1.35 ± 0.14 | 1.41 ± 0.24 | 1.57 ± 0.54 | 2.83 ± 1.02 |
| All | 1.49 ± 0.19 | 1.37 ± 0.27 | 1.72 ± 0.59 | 2.86 ± 0.95. |

Plasma concentration versus time profiles were best described by a two-compartment model with first order input and a lag time. Modeling was performed on individual data sets and observed and predicted concentration versus time plots were prepared using WINNONLIN® model 12. In some cases estimates of the terminal half-life ($T_{1/2\beta}$) were very large due to a few points in the terminal phase of the curve having concentrations that were similar or fluctuating, resulting in a flat slope. In many of these cases the large $T_{1/2\beta}$ produced a very large estimate for AUC. Other variations in parameter estimates from the model caused a few aberrant values in some parameter estimates. These values were not excluded from the data analysis or treated statistically as outliers. Instead, data are summarized by the median value rather than the mean. Thus the unusually high or low values remain in the data presented but do not exert undue influence on the group summary statistics.

Pharmacokinetic modeling results shown in Table 7 indicate that there was a lag time of approximately nine minutes following oral administration. By comparison, the lag time associated with inhaled 90/8/2 was negligible, less than 0.5 minutes. Furthermore, the absorption rate of inhaled 90/8/2 was faster (shorter $T_{1/2k01}$) than that following oral administration in the fasted state and approximately ten-fold faster than absorption in the fed state. The much shorter lag time and faster absorption rate following 90/8/2 inhalation account for the greater systemic exposure observed within the first 5 to 10 minutes after dosing compared to oral administration. The calculated parameter, time to reach 50% of $C_{max}$ ($T_{Cmax50}$) also indicates that 90/8/2 inhalation produced earlier levodopa systemic exposure than oral administration. With the exception of oral administration in the fed state, absorption was much faster than elimination.

Figure 6:
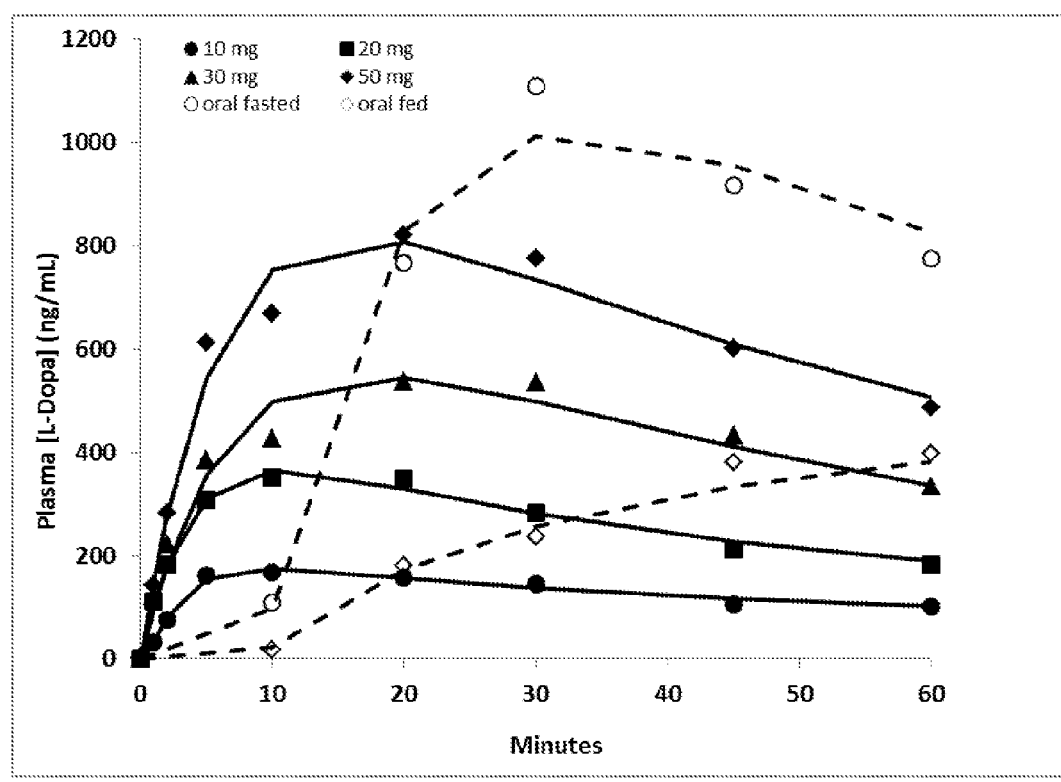
FIG. 6: Mean levodopa plasma concentrations with and without carbidopa (CD) pretreatment.

The combined effects of the lag time and absorption rates on plasma concentrations in the first few minutes following administration is illustrated in FIG. 6 which presents pharmacokinetic modeling of mean plasma concentration data. This plot shows concentrations predicted by the pharmacokinetic model for 90/8/2 inhalation and oral levodopa administration over the first sixty minutes following dosing. The symbols represent observed mean concentrations and the lines represent concentrations predicted by the pharmacokinetic model. The good correlation of predicted and observed values indicates that the model describes the data very well. The figure also illustrates the other observations from the study that 90/8/2 inhalation results in rapid increases in plasma levodopa concentrations, potentially clinically relevant plasma concentrations can be achieved within 5 to 10 minutes of dosing, and exposure is dose-proportional.

TABLE 7

Pharmacokinetic Parameters
(Median Values) Estimated by Pharmacokinetic Modeling

| Dose (mg) | $T_{lag}$(min) | $T_{1/2ko1}$(min) | $T_{1/2\alpha}$(min) | $T_{1/2\beta}$(min) |
|---|---|---|---|---|
| 90/8/2* | | | | |
| 10 | 0.21 | 4.31 | 8.18 | 180.33 |
| 20 | <0.01 | 3.53 | 11.54 | 135.04 |
| 30 | <0.01 | 5.47 | 33.38 | 167.66 |
| 50 | 0.29 | 7.37 | 26.12 | 142.46 |
| Oral | | | | |
| 100(fasted) | 9.41 | 9.96 | 9.64 | 132.40 |
| 100 (fed) | 9.78 | 65.39 | 7.49 | 98.21. |

*Refers to estimated fine particle dose

Figure 7:
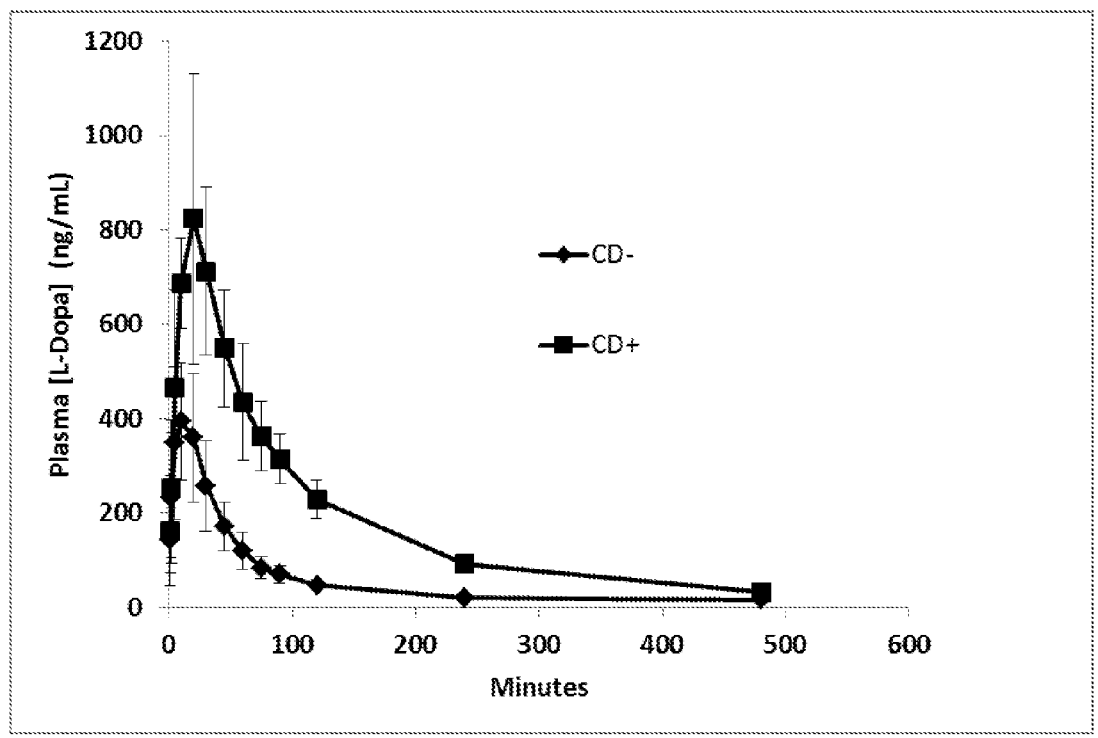
FIG. 7: Pharmacokinetic modeling of mean plasma concentrations. Symbols represent observed mean concentrations and lines represent concentrations predicted by the model.

Part B Plasma concentrations from Part B of the study in which 90/8/2, 40 mg levodopa FPD was inhaled with or without carbidopa pretreatment in a cross-over design are shown in FIG. 7. Peak plasma concentrations and exposure were higher with carbidopa pretreatment. Plasma levodopa clearance was approximately four-fold faster without CD pretreatment. Correspondingly, $C_{max}$ and AUC were lower and $T_{max}$ and $T_{1/2}$ were somewhat shorter without CD pretreatment (Table 8).

TABLE 8

Levodopa Pharmacokinetic Parameters
(Mean ± SD) Estimated by Non-compartmental Analysis Following
Inhalation of 40 mg 90/8/2 with and without Carbidopa Pretreatment.

| Treatment | $C_{max}$ ng/mL | $T_{max}$* min | $AUC_{0-\infty}$ ng-min/mL | CL/F mL/min | $T_{1/2}$* min |
|---|---|---|---|---|---|
| 40 mg with Carbidopa | 895 ± 276 | 20 | 95,058 ± 15,979 | 429 ± 59 | 113 |
| 40 mg without Carbidopa | 423 ± 126 | 8 | 27,005 ± 8,756 | 1,619 ± 504 | 85. |

*Median value

CONCLUSIONS

The main findings of this study were: (i) that inhaled 90/8/2 resulted in rapid increases in plasma levodopa concentrations; (ii) Systemic exposure to levodopa based on $C_{max}$ and AUC was much greater over the first 10 minutes after dosing with 90/8/2 inhalation compared to oral drug administration; (iii) Potentially therapeutically relevant plasma levodopa concentrations were achieved within 5 to 10 minutes after 90/8/2 doses of 20 to 50 mg levodopa fine particle dose in healthy adults; (iv) Subject to subject variability in plasma levodopa concentrations was considerably less following inhalation compared to oral administration; (v) Systemic levodopa exposure was proportional to levodopa fine particle dose administered; (vi) Pharmacokinetic modeling indicated that inhaled 90/8/2 had much shorter lag times and faster absorption rates than oral administration; vii) Dose-normalized (based on estimated fine particle dose) exposure following inhalation was 1.3 to 1.6 times greater based on AUC and 1.6 to 2.9 times greater based on $C_{max}$ compared to oral administration; and viii) Plasma levodopa clearance was approximately four-fold greater and levodopa exposure was reduced in the absence of carbidopa pre-treatment.

The patent and scientific literature referred to herein establishes the knowledge that is available to those with skill in the art. All United States patents and published or unpublished United States patent applications cited herein are incorporated by reference. All published foreign patents and patent applications cited herein are hereby incorporated by reference. All other published references, documents, manuscripts and scientific literature cited herein are hereby incorporated by reference.

While this invention has been particularly shown and described with references to preferred embodiments thereof, it will be understood by those skilled in the art that various changes in form and details may be made therein without departing from the scope of the invention encompassed by the appended claims. It should also be understood that the embodiments described herein are not mutually exclusive and that features from the various embodiments may be combined in whole or in part in accordance with the invention.

What is claimed is:

1. A method of reducing the inter-patient variability of levodopa in a patient population of Parkinson's disease patients comprising:
    administering levodopa by inhalation to a patient population of at least two patients suffering from Parkinson's disease;
    wherein the inter-patient variability of the levodopa plasma concentration at the time period of ten minutes post inhalation has less than a 50% coefficient of variation.

2. The method of claim 1, wherein said time period is 30 minutes.

3. The method of claim 1, wherein said time period is 60 minutes.

4. The method of claim 1, wherein said patients are stage 2, stage 3 or stage 4 Parkinson's disease patients.

5. The method of claim 1, wherein said coefficient of variation is less than 35%.

6. The method of claim 1, wherein said dosage given by inhalation provides a higher plasma concentration at ten minutes as compared to an equivalent dose of levodopa given orally.

7. A method of reducing the inter-patient variability of levodopa in a patient population of Parkinson's disease patients comprising:
    administering levodopa by inhalation to a patient population of at least two patients suffering from Parkinson's disease;
    wherein the inter-patient variability of the levodopa AUC at the time period of ten minutes post inhalation has less than a 50% coefficient of variation.

8. The method of claim 7, wherein said time period post inhalation is 30 minutes.

9. The method of claim 7, wherein said time period post inhalation is 60 minutes.

10. The method of claim 7, wherein said patients are stage 2, stage 3 or stage 4 Parkinson's disease patients.

11. The method of claim 7, wherein said coefficient of variation is less than 35%.

12. The method of claim 7, wherein said patient does not require dose titration of levodopa.

13. The method of claim 7, wherein said dosage given by inhalation provides a higher AUC at ten minutes as compared to an equivalent dose of levodopa given orally.

14. The method of claim 1, wherein the patient does not require co-administration of a DOPA decarboxylase inhibitor.

15. The method of claim 1, wherein the patient is co-administered a lower dosage of DOPA decarboxylase inhibitor as compared to the dosage of DOPA decarboxylase inhibitor co-administered to a patient receiving orally administered L-Dopa.

16. The method of claim 1, wherein the patient is co-administered a dosage of a DOPA decarboxylase inhibitor less frequently as compared to frequency of co-administration of a DOPA decarboxylase inhibitor to a patient receiving orally administered L-Dopa.

17. The method of claim 14, 15 or 16, wherein the DOPA decarboxylase inhibitor is carbidopa or benserazide.

18. The method of claim 1 or 7, wherein the dose of levodopa comprises 90% by dry weight levodopa, 8% by dry weight dipalmitoylphosphatidylcholine (DPPC) and 2% sodium chloride.

19. A method of providing rapid relief of motor fluctuations in a Parkinson's disease patient population comprising:
    administering at least one dose of levodopa by inhalation to a first Parkinson's disease patient who takes a first average daily dose of oral levodopa;
    administering at least one dose of levodopa by inhalation to a second Parkinson's disease patient who takes a second average daily dose of oral levodopa;
    wherein both patients have a reduction in motor symptoms within 20 minutes of administration of said levodopa by inhalation upon administration of the same dose of pulmonary levodopa; and
    wherein the inter-patient variability of the levodopa plasma concentration at the time period of ten minutes post inhalation has less than a 50% coefficient of variation.

20. The method of claim 19, wherein said first average daily dose of oral levodopa is higher than the second average daily dose of oral levodopa.

21. The method of claim 19, wherein said first average daily dose of oral levodopa is higher than the second average daily dose of oral levodopa and both average daily doses range from 200 mg to 2500 mg of levodopa.

22. The method of claim 19, wherein said first average daily dose of levodopa between 400-700 mg.

23. The method of claim 19, wherein said second average daily dose of levodopa is between 700-2000 mg.

24. The method of claim 20, wherein said first average daily dose of levodopa between 400-700 mg.

25. The method of claim 19, wherein said second average daily dose of levodopa is between 1000-2000 mg.

26. The method of claim 19, wherein said method further comprises administering said pulmonary levodopa to more than two patients wherein said patients take multiple different average daily oral doses of levodopa ranging from 200 mg to 3000 per day.

* * * * *